(12) United States Patent
Fadli

(10) Patent No.: US 8,491,669 B2
(45) Date of Patent: Jul. 23, 2013

(54) CATIONIC 4-AMINOPYRIDINE, DYE COMPOSITION COMPRISING A CATIONIC 4-AMINOPYRIDINE, PROCESSES THEREFOR AND USES THEREOF

(75) Inventor: Aziz Fadli, Chelles (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/514,560

(22) PCT Filed: Dec. 3, 2010

(86) PCT No.: PCT/EP2010/068801
§ 371 (c)(1),
(2), (4) Date: Aug. 27, 2012

(87) PCT Pub. No.: WO2011/069898
PCT Pub. Date: Jun. 16, 2011

(65) Prior Publication Data
US 2013/0048007 A1     Feb. 28, 2013

Related U.S. Application Data

(60) Provisional application No. 61/292,253, filed on Jan. 5, 2010.

(30) Foreign Application Priority Data

Dec. 7, 2009 (FR) .................................. 09 58716

(51) Int. Cl.
*A61Q 5/10* (2006.01)
*C07D 211/02* (2006.01)

(52) U.S. Cl.
USPC ............. 8/405; 8/409; 8/435; 8/568; 546/249

(58) Field of Classification Search
USPC ................... 8/405, 409, 435, 568; 546/249
See application file for complete search history.

(56) References Cited

U.S. PATENT DOCUMENTS 7,258,702 B2 * 8/2007 Eliu et al. ................. 8/405

OTHER PUBLICATIONS

STIC Search Report dated Jan. 14, 2013.*

* cited by examiner

*Primary Examiner* — Eisa Elhilo
(74) *Attorney, Agent, or Firm* — John A. Artz; Dickinson Wright PLLC

(57) ABSTRACT

The present invention relates to a cationic aminopyridine of general formula (I), acid-addition salts thereof and solvates thereof: in which: $R_1$ is a linear or branched, saturated $C_1$-$C_{20}$ alkyl radical, substituted and/or interrupted with a cationic radical. The present invention is also directed towards a process for synthesizing this cationic aminopyridine, compositions, uses, hair dyeing processes and devices using this cationic aminopyridine.

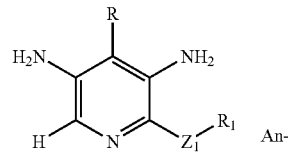

(I)

16 Claims, No Drawings

CATIONIC 4-AMINOPYRIDINE, DYE COMPOSITION COMPRISING A CATIONIC 4-AMINOPYRIDINE, PROCESSES THEREFOR AND USES THEREOF

This application is a national phase application based on PCT/EP2010/068801 filed Dec. 3, 2010, which claims priority from French Application No. 0958716, filed Dec. 7, 2009, and claims the benefit of U.S. Provisional Application No. 61/292,253, filed on Jan. 5, 2010, the content of all of which is incorporated herein by reference in their entirety.

TECHNICAL FIELD

The present invention relates to novel cationic aminopyridines, to their use for dyeing keratin fibres, in particular human keratin fibres such as the hair, to dye compositions comprising such cationic aminopyridines, and to processes and devices using these cationic aminopyridines.

BACKGROUND

It is known practice to dye keratin fibres, and in particular human hair, with dye compositions containing oxidation dye precursors, which are generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds via a process of oxidative condensation.

It is also known that the shades obtained with these oxidation bases can be varied by combining them with couplers or coloration modifiers, the latter being chosen especially from aromatic meta-diaminobenzenes, meta-aminophenols, meta-diphenols and certain heterocyclic compounds such as indole compounds.

The variety of molecules used as oxidation bases and couplers allows a wide range of colours to be obtained.

The "permanent" coloration obtained by means of these oxidation dyes must moreover satisfy a certain number of requirements. Thus, it must have no toxicological drawbacks, it must allow shades to be obtained in the desired intensity and it must show good remanence with respect to external agents such as light, bad weather, washing, permanent-waving, perspiration and rubbing.

The dyes must also allow grey hair to be covered, and they must be as unselective as possible, i.e. they must produce the smallest possible coloration differences along the same length of a keratin fibre, which is generally differently sensitized (i.e. damaged) between its end and its root.

SUMMARY OF THE INVENTION

The Applicant has discovered, surprisingly and advantageously, a novel family of heterocyclic couplers formed from cationic aminopyridines. These couplers can produce novel compositions for dyeing keratin fibres, which are capable of giving colorations in varied, powerful, chromatic shades.

These compositions are also sparingly selective and are fast: they show good resistance to the various attacking factors to which the fibres may be subjected, and especially to repeated washing and to light.

Moreover, these heterocyclic couplers show good solubility, allowing satisfactory uptake of the colour.

DESCRIPTION OF THE PREFERRED EMBODIMENTS

Patent application FR 2 874 821 describes the use of an aminopyridine: 4-[(3,5-diaminopyridin-2-yl)]-1,1-dimethylpiperazin-1-ium methyl sulfate of formula:

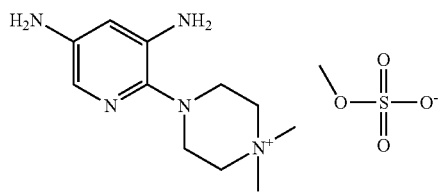

as an intermediate in the synthesis of a heteroaromatic dinuclear direct dye.

A first subject of the invention concerns a family of cationic aminopyridines and processes for synthesizing them.

A subject of the invention is also a composition containing at least one cationic aminopyridine, dyeing processes using this composition, the uses of the said composition according to the present invention for dyeing keratin fibres, in particular human keratin fibres such as the hair, and multi-compartment devices or dyeing "kits".

Other characteristics, aspects, subjects and advantages of the present invention will emerge even more clearly on reading the description and the examples that follow.

The present invention relates to a cationic aminopyridine chosen from:

the compounds of general formula (I'), acid-addition salts thereof and solvates thereof:

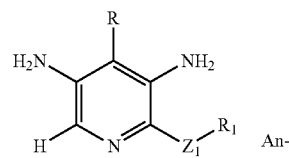

in which the group $Z_1R_1$ is cationic, $Z_1$ is an oxygen atom or a group $NR_2$;

$R_2$ is a hydrogen atom or a linear or branched $C_1$-$C_4$ alkyl radical, a benzyl radical or an acetyl radical;

$R_1$ is a linear or branched saturated $C_1$-$C_{10}$ alkyl radical, substituted or interrupted with a cationic radical, optionally interrupted with one or more oxygen atoms and/or with one or more groups $NR_2$, optionally substituted with one or more radicals chosen from hydroxyl and $C_1$-$C_4$ alkoxy or hydroxyalkyl radicals, the said cationic radical being a linear, branched or cyclic, saturated or unsaturated radical, comprising a quaternary ammonium; or $R_1$ is a saturated, unsaturated or aromatic, 5- to 8-membered cationic heterocycle optionally substituted with one or more radicals chosen from $C_1$-$C_4$ alkyl, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals; when $Z_1$ represents $NR_2$, then $R_1$ and $R_2$ may form, together with the nitrogen atom to which they are attached, an unsaturated 5- to 8-membered cationic heterocycle, optionally substituted with one or more radicals chosen from $C_1$-$C_{10}$ alkyl, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals, this heterocycle possibly containing one or more heteroatoms chosen from N and O, preferably N, or $R_1$ and $R_2$ may form, together with the nitrogen atom to which they are attached, an unsaturated 5- to 8-membered non-cationic heterocycle, substituted with a cationic radical and optionally substituted with one or more radicals chosen from $C_1$-$C_{10}$ alkyl, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals; the said cationic radical being a linear, branched or cyclic, saturated or unsaturated radical, comprising a quaternary ammonium;

R is chosen from a hydrogen atom, halogens chosen from fluorine, chlorine and bromine, and linear or branched $C_1$-$C_4$ alkyl, carboxyl (—COOH) and ($C_1$-$C_4$)alkoxycarbonyl radicals, An—represents an anion or a mixture of anions, the following compounds, acid-addition salts thereof and solvates thereof:

1-(3,5-diaminopyridin-2-yl)-N,N,N-trimethylpyrrolidine-3-ammonium, 4-(3,5-diaminopyridin-2-yl)-1-(2-hydroxyethyl)-1-methylpiperazine-1-ium, 4-(3,5-diaminopyridin-2-yl)-1,1-bis(2-hydroxyethyl)piperazine-1-ium, 4-(3,5-diaminopyridin-2-yl)(2-trimethylethane)morpholineammonium, 4-(3,5-diaminopyridin-2-yl)(2-trimethylmethane)morpholineammonium, 4-(3,5-diaminopyridin-2-yl)(2-methyldiethylethane)morpholineammonium, 4-(3,5-diaminopyridin-2-yl)(2-methyldiethylmethane)morpholineammonium, 4-(3,5-diaminopyridin-2-yl)-2-morpholine-1,1-dimethylpyrrolidinium, (3,5-diaminopyridin-2-yl)-3-trimethylpiperidineammonium, (3,5-diaminopyridin-2-yl)-4-trimethylpiperidineammonium.

In the context of the invention, the term "cationic radical" present in the compound of formula (I) or (I') as defined later means any linear, branched or cyclic, saturated or unsaturated radical, comprising a quaternary ammonium, this quaternary ammonium preferably being of the type —N$^+$RaRbRc, with Ra, Rb and Rc, which may be identical or different, representing a $C_1$-$C_6$ alkyl radical that may be substituted with a hydroxyl. Ra and Rb may form, together with the nitrogen atom to which they are attached, a saturated or unsaturated 5- to 8-membered cationic heterocycle, the radical Rc, when it is present, then being a $C_1$-$C_6$ alkyl radical that may be substituted with a hydroxyl. The cationic radical may also be N,N-dimethylpiperazinium.

When the cationic radical present in the compound of formula (I) or (I') comprises a quaternary ammonium of the type —N$^+$RaRbRc, and when Ra and Rb form, together with the nitrogen atom to which they are attached, an unsaturated cationic heterocycle such as a pyridinium, then the quaternary ammonium does not bear a group Rc.

Examples of quaternary ammoniums of the type —N$^+$RaRbRc that may be mentioned include trimethylammonium, triethylammonium, dimethylethylammonium, diethylmethylammonium, diisopropylmethylammonium, diethylpropylammonium, hydroxyethyldiethylammonium, di-β-hydroxyethylmethylammonium, tri-β-hydroxyethylammonium, N-methylpiperidinium, N-methylpyrrolidinium, N-methylmorpholinium, imidazolium, hydroxyethylimidazolium, methylimidazolium and N-methylpiperazinium radicals.

For the purposes of the present patent application, the term "cationic heterocycle" means a 5- to 8-membered heterocycle in which at least one of the ring members is a quaternary ammonium.

Examples of cationic heterocyclic radicals that may be mentioned include imidazolium, pyridinium, piperidinium, piperazinium, pyrrolidinium, morpholinium, pyrimidinium, thiazolium, benzimidazolium, benzothiazolium, oxazolium, benzotriazolium, pyrazolium, triazolium and benzoxazolium radicals.

Preferably, $Z_1$ represents a group $NR_2$ with $R_2$ chosen from a hydrogen atom and a $C_1$-$C_2$ alkyl radical, and more preferentially $NR_2$ is chosen from NH and NMe.

Preferably, $R_1$ is a $C_1$-$C_8$ alkyl radical substituted or interrupted with a cationic radical as defined previously, optionally interrupted with one or more oxygen atoms and/or with one or more groups $NR_2$, optionally substituted with a hydroxyl radical.

Preferably, the cationic radicals are chosen from trimethylammonium, triethylammonium, dimethylethylammonium, diethylmethylammonium, diisopropylmethylammonium, hydroxyethyldiethylammonium, imidazolium, pyridinium, pyrimidinium, thiazolium and benzimidazolium radicals.

Even more preferably, the cationic radicals are chosen from trimethylammonium and imidazolium radicals.

According to a first particularly preferred variant of the invention, $Z_1$ is an oxygen atom or $NR_2$ with $R_2$ chosen from hydrogen and a linear or branched $C_1$-$C_4$ alkyl radical, preferably $R_2$ represents H or Me; and $R_1$ represents a saturated linear $C_2$-$C_8$ alkyl radical, optionally interrupted with an oxygen atom or with a group NH, optionally substituted with a hydroxyl radical, and substituted or interrupted with a cationic radical chosen from trimethylammonium and imidazolium radicals.

According to a second preferred variant of the invention, $Z_1$ is a group $NR_2$ and $R_1$ and $R_2$ form, together with the nitrogen atom to which they are attached, a saturated or unsaturated 5- to 8-membered cationic heterocycle, optionally substituted with one or more radicals chosen from $C_1$-$C_{10}$ alkyl and $C_1$-$C_{10}$ hydroxyalkyl radicals. This heterocycle may contain one or more heteroatoms chosen from N and O, preferably N. According to this variant, $Z_1$ is a group $NR_2$ and $R_1$ and $R_2$ form, together with the nitrogen atom to which they are attached, a piperidinium, imidazolium, pyrrolidinium, morpholinium or piperazinium radical substituted with one or more radicals chosen from $C_1$-$C_4$ hydroxyalkyl and $C_1$-$C_4$ alkyl radicals.

According to a third variant, $Z_1$ is a group $NR_2$ and $R_1$ and $R_2$ form, together with the nitrogen atom to which they are attached, a saturated or unsaturated 5- to 8-membered non-cationic heterocycle, substituted with a cationic radical as defined previously, preferably chosen from trimethylammonium, diethylmethylammonium and imidazolium radicals. According to this variant, the saturated or unsaturated 5- to 8-membered non-cationic heterocycle is preferably chosen from pyrrolidinine, piperidine and morpholine, this ring being substituted with a cationic radical chosen from trimethylammonium, diethylmethylammonium and imidazolium radicals.

Preferably, R is chosen from a hydrogen atom and $C_1$-$C_4$ alkyl radicals. Even more preferably, R is a hydrogen atom.

The cationic aminopyridines of the invention may be present in free form or in the form of salts, such as addition salts with a mineral acid preferably chosen from hydrochlorides, hydrobromides, sulfates, or phosphates, or with an organic acid, for instance citrates, succinates, tartrates, lactates, tosylates, benzenesulfonates, acetates, para-toluenesulfonates, formates or methanesulfonates.

The cationic aminopyridines of the invention may also be in the form of solvates, for example a hydrate or a solvate of a linear or branched alcohol such as ethanol or isopropanol.

In the context of the invention, the term "cationic aminopyridines of the invention" means any mesomeric or isomeric form.

The electrical neutrality of the cationic aminopyridines of the invention is ensured by one or a mixture of cosmetically acceptable organic or mineral anions, noted An-.

An—represents an anion or a mixture of anions chosen, for example, from a halide, such as chloride, bromide, fluoride or iodide; a hydroxide; a sulfate; a hydrogen sulfate; an alkyl sulfate for which the linear or branched alkyl part is $C_1$-$C_6$, for instance the methyl sulfate or ethyl sulfate ion; carbonates and hydrogen carbonates; carboxylic acid salts such as formate, acetate, citrate, tartrate or oxalate; alkylsulfonates for which the linear or branched alkyl part is $C_1$-$C_6$, for instance the methylsulfonate ion; arylsulfonates for which the aryl part, preferably phenyl, is optionally substituted with one or more $C_1$-$C_4$ alkyl radicals, for instance 4-tolylsulfonate; alkylsulfonyls such as mesylate.

Preferably, the cationic aminopyridines of the invention are chosen from the following compounds:

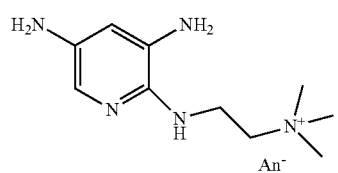

(compound 1)

2-[(3,5-diaminopyridin-2-yl)amino]-N,N,N-trimethylethaneammonium, An-

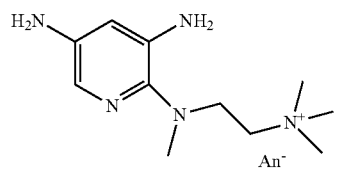

(compound 2)

2-[(3,5-diaminopyridin-2-yl)(methyl)amino]-N,N,N-trimethylethaneammonium, An-

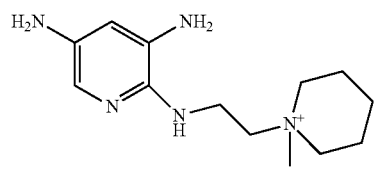

(compound 3)

1-{2-[(3,5-diaminopyridin-2-yl)amino]ethyl}-1-methylpiperidinium, An-

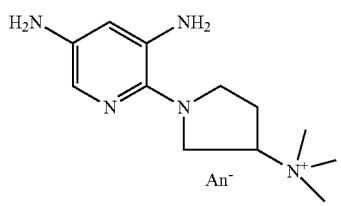

(compound 4)

1-(3,5-diaminopyridin-2-yl)-N,N,N-trimethylpyrrolidine-3-ammonium, An-

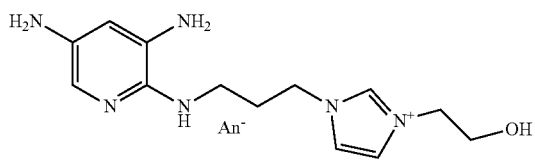

(compound 5)

1-{3-[(3,5-diaminopyridin-2-yl)amino]propyl}-3-(2-hydroxyethyl)-1H-imidazol-3-ium, An-

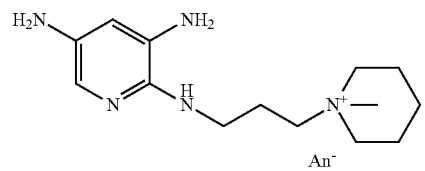

(compound 6)

1-{3-[(3,5-diaminopyridin-2-yl)amino]propyl}-1-methylpiperidinium, An-

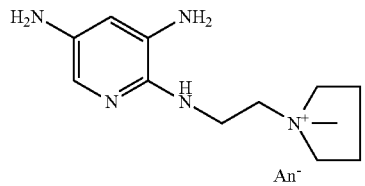

(compound 7)

1-{2-[(3,5-diaminopyridin-2-yl)amino]ethyl}-1-methylpyrrolidinium, An-

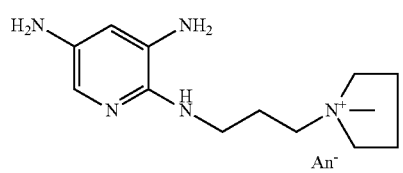

(compound 8)

1-{3-[(3,5-diaminopyridin-2-yl)amino]propyl}-1-methylpyrrolidinium, An-

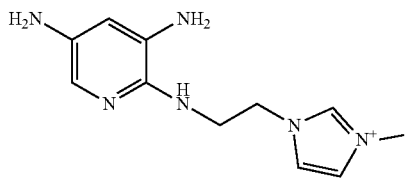

(compound 9)

1-{2-[(3,5-diaminopyridin-2-yl)amino]ethyl}-3-methyl-1H-imidazol-3-ium, An-

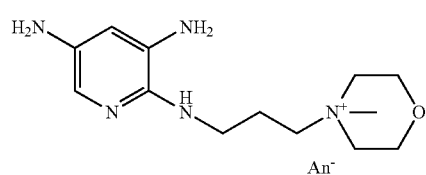

(compound 10)

4-{3-[(3,5-diaminopyridin-2-yl)amino]propyl}-4-methylmorpholin-4-ium, An-

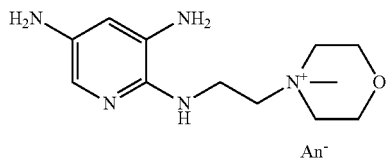

(compound 11)

4-{2-[(3,5-diaminopyridin-2-yl)amino]ethyl}-4-methylmorpholin-4-ium, An-

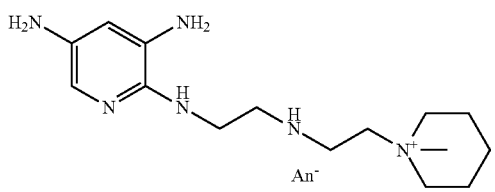

(compound 12)

1-[2-({2-[(3,5-diaminopyridin-2-yl)amino]ethyl}amino)ethyl]-1-methylpiperidinium, An-

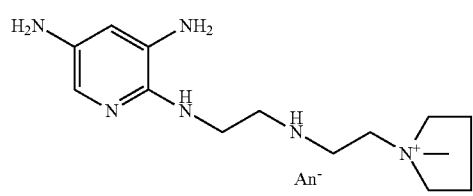

(compound 13)

1-[2-({2-[(3,5-diaminopyridin-2-yl)amino]ethyl}amino)ethyl]-1-methylpyrrolidinium, An-

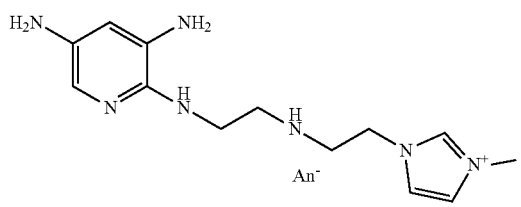

(compound 14)

1-[2-({2-[(3,5-diaminopyridin-2-yl)amino]ethyl}amino)ethyl]-3-methyl-1H-imidazol-3-ium, An-

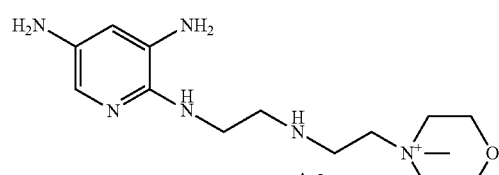

(compound 15)

4-[2-({2-[(3,5-diaminopyridin-2-yl)amino]ethyl}amino)ethyl]-4-methylmorpholin-4-ium, An-

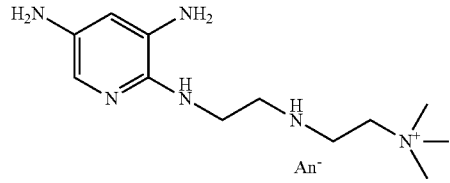

(compound 16)

2-({2-[(3,5-diaminopyridin-2-yl)amino]ethyl}amino)-N,N,N-trimethylethaneammonium, An-

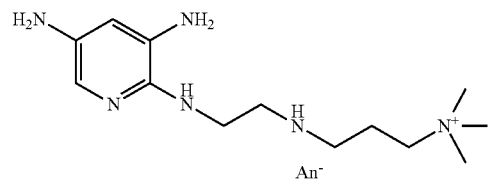

(compound 17)

3-({2-[(3,5-diaminopyridin-2-yl)amino]ethyl}amino)-N,N,N-trimethylpropane-1-ammonium, An-

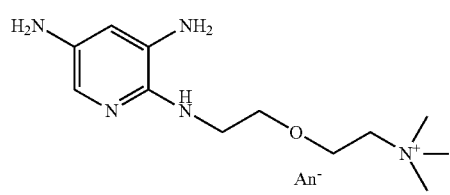

(compound 18)

2-{2-[(3,5-diaminopyridin-2-yl)amino]ethoxy}-N,N,N-trimethylethaneammonium, An- (compound 19)

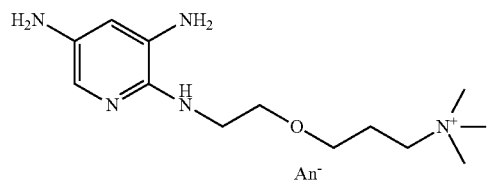

3-{2-[(3,5-diaminopyridin-2-yl)amino]ethoxy}-N,N,N-trimethylpropane-1-ammonium, An- (compound 20)

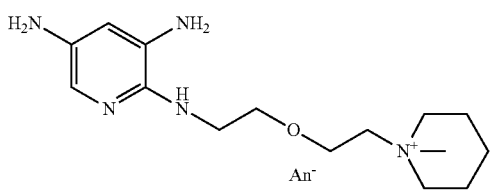

1-(2-{2-[(3,5-diaminopyridin-2-yl)amino]ethoxy}ethyl)-1-methylpiperidinium, An- (compound 21)

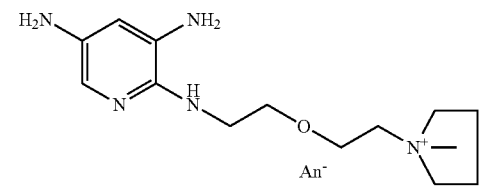

1-(2-{2-[(3,5-diaminopyridin-2-yl)amino]ethoxy}ethyl)-1-methylpyrrolidinium, An- (compound 22)

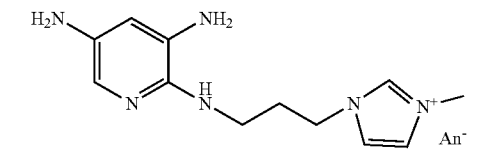

1-{3-[(3,5-diaminopyridin-2-yl)amino]propyl}-3-methyl-1H-imidazol-3-ium, An- (compound 23)

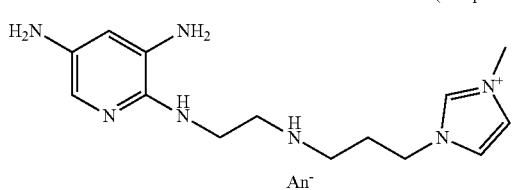

1-[3-({2-[(3,5-diaminopyridin-2-yl)amino]ethyl}amino)propyl]-3-methyl-1H-imidazol-3-ium, An- (compound 24)

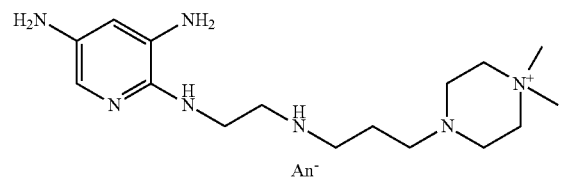

4-[3-({2-[(3,5-diaminopyridin-2-yl)amino]ethyl}amino)propyl]-1,1-dimethylpiperazin-1-ium, An- (compound 25)

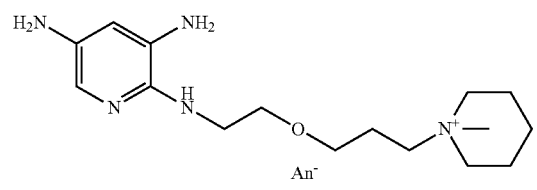

1-(3-{2-[(3,5-diaminopyridin-2-yl)amino]ethoxy}propyl)-1-methylpiperidinium, An- (compound 26)

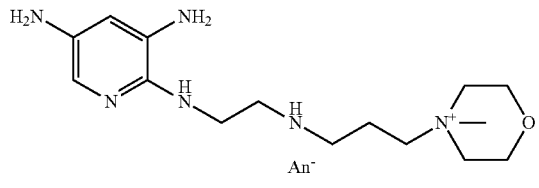

4-[3-({2-[(3,5-diaminopyridin-2-yl)amino]ethyl}amino)propyl]-4-methylmorpholin-4-ium, An- (compound 27)

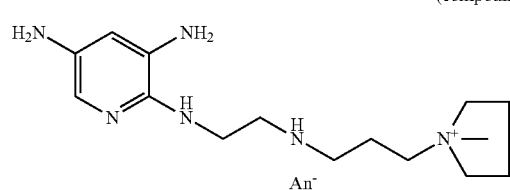

1-[3-({2-[(3,5-diaminopyridin-2-yl)amino]ethyl}amino)propyl]-1-methylpyrrolidium, An- (compound 26bis)

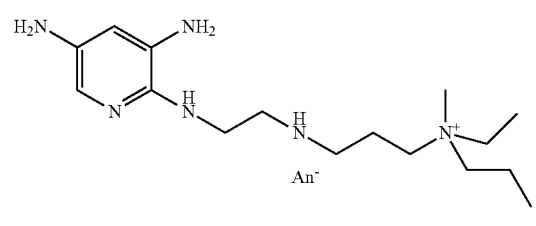

3-({2-[(3,5-diaminopyridin-2-yl)amino]ethyl}amino)-N-ethyl-N-methyl-N-propylpropane-1-ammonium

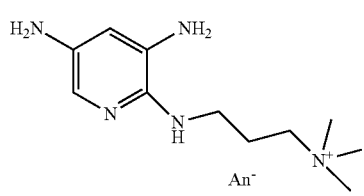
(compound 28)

3-[(3,5-diaminopyridin-2-yl)amino]-N,N,N-trimethylpropane-1-ammonium, An-

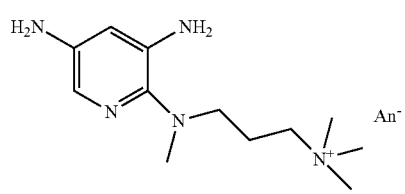
(compound 29)

3-[(3,5-diaminopyridin-2-yl)(methyl)amino]-N,N,N-trimethylpropane-1-ammonium, An-

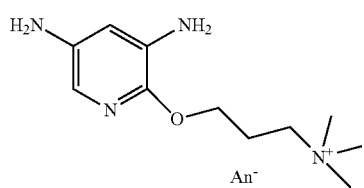
(compound 30)

3-[(3,5-diaminopyridin-2-yl)oxy]-N,N,N-trimethylpropane-1-ammonium, An-

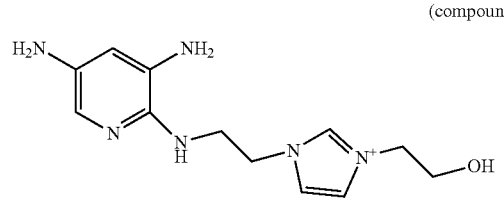
(compound 31)

1-{2-[(3,5-diaminopyridin-2-yl)amino]ethyl}-3-(2-hydroxyethyl)-1H-imidazol-3-ium, An-

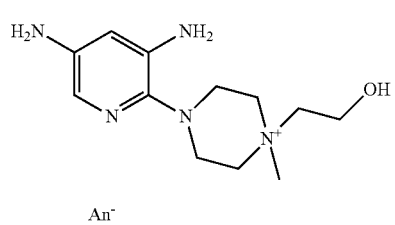
(compound 32)

4-(3,5-diaminopyridin-2-yl)-1-(2-hydroxyethyl)-1-methylpiperazin-1-ium, An-

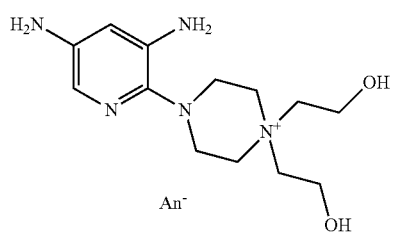
(compound 33)

4-(3,5-diaminopyridin-2-yl)-1,1-bis(2-hydroxyethyl)piperazin-1-ium, An-

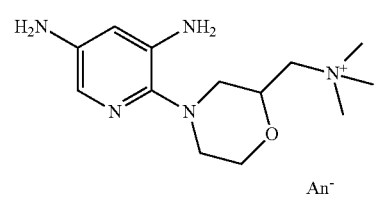
(compound 34)

4-(3,5-diaminopyridin-2-yl)(2-trimethylmethane)morpholine-ammonium, An-

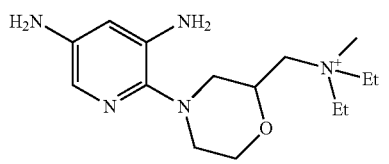
(compound 35)

4-(3,5-diaminopyridin-2-yl)(2-methyldiethylmethane)morpholine-ammonium, An-

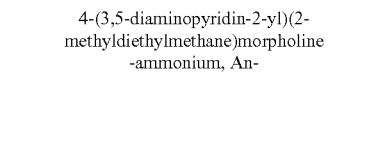
(compound 34bis)

4-(3,5-diaminopyridin-2-yl)(2-trimethylethane)morpholineammonium, An-

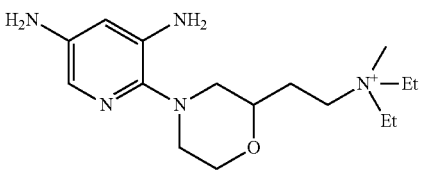
(compound 35bis)

4-(3,5-diaminopyridin-2-yl)(2-methyldiethylethane)morpholine-ammonium, An-

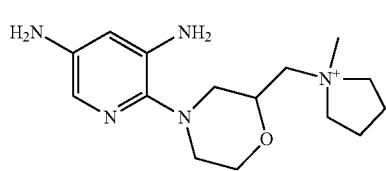

4-(3,5-diaminopyridin-2-yl)-2-
morpholine-1,1-
dimethylpyrrolidinium, An⁻

(compound 36)

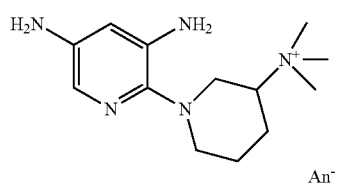

(3,5-diaminopyridin-2-yl)-3-
trimethylpiperidineammonium,
An⁻

(compound 37)

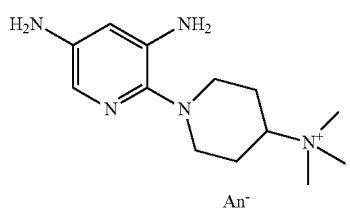

(3,5-diaminopyridin-2-yl)-4-
trimethylpiperidineammonium,
An⁻

(compound 38)

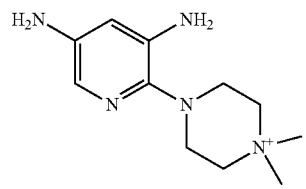

4-(3,5-diaminopyridin-2-yl)-1,1-
dimethylpiperazin-1-ium, An⁻

(compound 39)

An⁻—having the same meaning as previously.

The cationic aminopyridines of the invention may be prepared according to various synthetic routes.

The present patent application also relates to the compounds of formula (II):

(II)

[structure of formula (II): pyridine with R, two $NO_2$ groups, H, and $S(O)_x$Me substituents]

in which R is chosen from a hydrogen atom, halogens chosen from fluorine, chlorine and bromine, and linear or branched $C_1$-$C_4$ alkyl, carboxyl (—COOH) and ($C_1$-$C_4$) alkoxycarbonyl radicals, and x represents 1 or 2.

These compounds may be used especially as intermediates in the synthesis of the cationic aminopyridines according to the invention.

More particularly, the present patent application also relates to a process for synthesizing a cationic aminopyridine according to the invention, starting with a compound of formula (III):

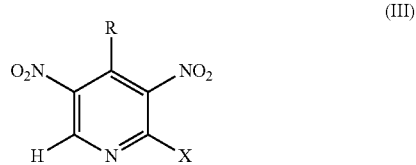

(III)

in which X represents a halogen or a group $SO_2R_3$ with $R_3$ chosen from $C_1$-$C_4$ alkyls, preferably methyl, a phenyl radical and a methylphenyl radical, and R is chosen from a hydrogen atom, halogens chosen from fluorine, chlorine and bromine, and linear or branched $C_1$-$C_4$ alkyl, carboxyl (—COOH) and ($C_1$-$C_4$)alkoxycarbonyl radicals, the said process comprising at least the following steps, in this order:

substitution of the group X with a group $Z_1R_1$ as defined above, reduction of the nitro groups.

This process is summarized in the scheme below:

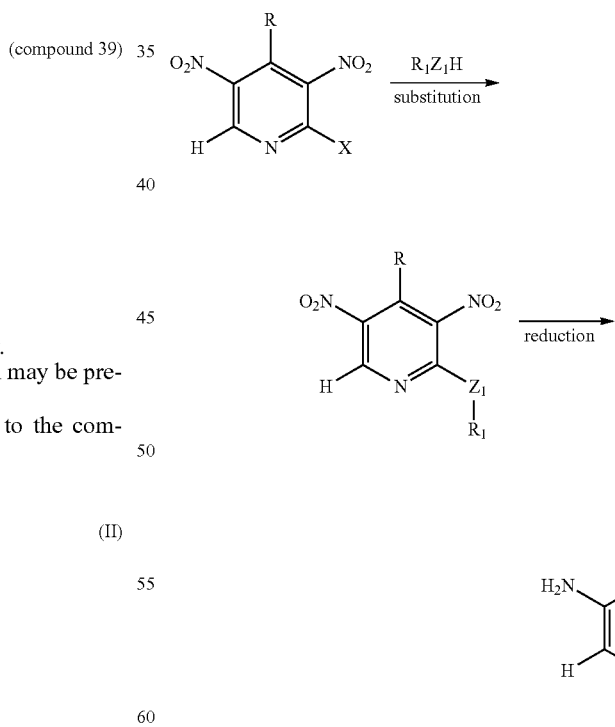

By way of example, when $R_1$ represents a $C_1$-$C_{10}$ alkyl radical substituted with a cationic radical, the said alkyl radical being interrupted with one or more oxygen atoms and/or with one or more groups $NR_2$, then the synthetic process used may be following:

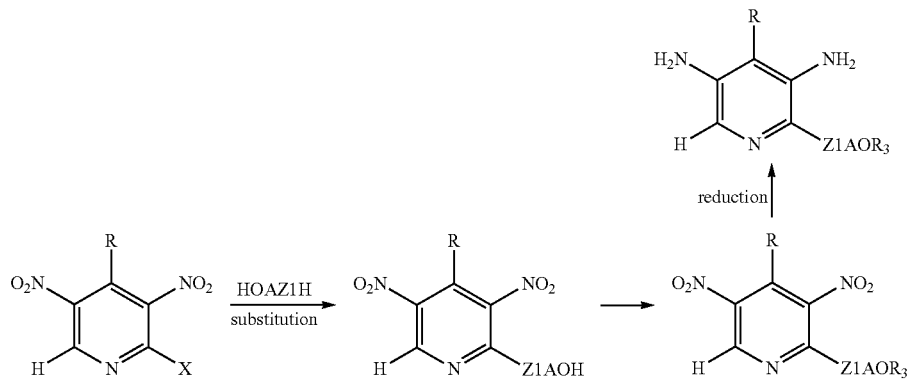

The substitution reaction is performed in a dipolar solvent such as acetonitrile or THF or in DMF or NMP, or in an alcohol such as ethanol, in the presence of a base such as triethylamine, ethyldiisopropylamine, sodium hydroxide or potassium hydroxide, for example, and one or more HOAZ1H for 1 to 24 hours at a temperature, from 20° C. to the reflux temperature of the solvent.

The hydroxyl function thus introduced is then substituted with a halide (for example mesyl or tosyl halide) in a solvent such as acetonitrile, THF or in an alcohol such as ethanol, for example, in the presence of a base such as triethylamine, ethyldiisopropylamine, sodium hydroxide or potassium hydroxide, for example, for 1 to 24 hours at a temperature from 20° C. to the reflux temperature of the solvent.

The substitution of the leaving group introduced in the preceding step is performed either by reaction with an aromatic tertiary amine such as methylimidazole to give the cationic compounds directly, or by reaction with a particular primary or secondary amine, for instance N,N-dimethylethylenediamine or 2-piperidin-1-ylethanamine to give compounds that are alkylated with at least one equivalent of an alkyl halide or methyl sulfate in a solvent such as THF, acetonitrile, dioxane or ethyl acetate, for 15 minutes to 24 hours at a temperature ranging from 15° C. to the reflux temperature of the solvent, to give the cationic nitro compounds.

The reduction of the nitro group of these compounds is performed under standard conditions, for example by performing a hydrogenation reaction under heterogeneous catalysis in the presence of Pd/C, Pd(II)/C, Ni/Ra, etc., or alternatively by performing a reduction reaction with a metal, for example with zinc, iron, tin, etc. (see *Advanced Organic Chemistry*, 3rd edition, J. March, 1985, Wiley Interscience, and *Reduction in Organic Chemistry*, M. Hudlicky, 1983, Ellis Horwood Series Chemical Science).

The present patent application also relates to the uses of a cationic aminopyridine of general formula (I), the acid-addition salts thereof and the solvates thereof:

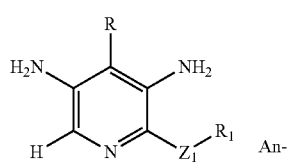

(I)

in which the group $Z_1R_1$ is cationic,
$Z_1$ is an oxygen atom or a group $NR_2$;

$R_2$ is a hydrogen atom, a linear or branched $C_1$-$C_4$ alkyl radical, a benzyl radical or an acetyl radical;

$R_1$ is a linear or branched saturated $C_1$-$C_{10}$ alkyl radical, substituted or interrupted with a cationic radical, optionally interrupted with one or more oxygen atoms and/or with one or more groups $NR_2$, optionally substituted with one or more radicals chosen from hydroxyl and $C_1$-$C_4$ alkoxy or hydroxyalkyl radicals, the said cationic radical being a linear or branched or cyclic, saturated or unsaturated radical, comprising a quaternary ammonium; or $R_1$ is a saturated, unsaturated or aromatic, 5- to 8-membered cationic heterocycle optionally substituted with one or more radicals chosen from $C_1$-$C_4$ alkyl, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals;

when $Z_1$ represents $NR_2$, then
$R_1$ and $R_2$ may form, together with the nitrogen atom to which they are attached, a saturated or unsaturated 5- to 8-membered cationic heterocycle, at least one of the ring members of which is a quaternary ammonium, optionally substituted with one or more radicals chosen from $C_1$-$C_{10}$ alkyl, hydroxyl, $C_1$-$C_4$ alkoxy, amino, ($C_1$-$C_4$) alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals, this heterocycle possibly containing one or more heteroatoms chosen from N and O, preferably N, or $R_1$ and $R_2$ may form, together with the nitrogen atom to which they are attached, a saturated or unsaturated 5- to 8-membered non-cationic heterocycle, substituted with a cationic radical and optionally substituted with one or more radicals chosen from $C_1$-$C_{10}$ alkyl, hydroxyl, $C_1$-$C_4$ alkoxy, amino, ($C_1$-$C_4$)alkylamino, di($C_1$-$C_4$) alkylamino, thio, ($C_1$-$C_4$)alkylthio, carboxyl, ($C_1$-$C_4$) alkylcarbonyl, sulfonyl, amido and $C_1$-$C_4$ hydroxyalkyl radicals; the said cationic radical being a linear or branched or cyclic, saturated or unsaturated radical, comprising a quaternary ammonium;

R is chosen from a hydrogen atom, halogens chosen from fluorine, chlorine and bromine, and linear or branched $C_1$-$C_4$ alkyl, carboxyl (—COOH) and ($C_1$-$C_4$)alkoxycarbonyl radicals, An— represents an anion or a mixture of anions, as a coupler for the dyeing of keratin fibres, especially human keratin fibres such as the hair.

The present patent application also relates to a cosmetic composition for dyeing, especially keratin fibres such as the hair, comprising, in a suitable dyeing medium, at least one cationic aminopyridine of general formula (I), an acid-addition salt thereof and/or a solvate thereof:

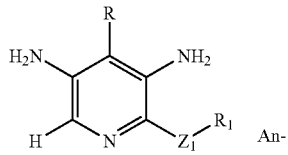

in which the group $Z_1R_1$ is cationic, $Z_1$ is an oxygen atom or a group $NR_2$;

$R_2$ is a hydrogen atom, a linear or branched $C_1$-$C_4$ alkyl radical, a benzyl radical or an acetyl radical;

$R_1$ is a linear or branched saturated $C_1$-$C_{10}$ alkyl radical, substituted or interrupted with a cationic radical, optionally interrupted with one or more oxygen atoms and/or with one or more groups $NR_2$, optionally substituted with one or more radicals chosen from hydroxyl and $C_1$-$C_4$ alkoxy or hydroxyalkyl radicals or $R_1$ is a saturated, unsaturated or aromatic, 5- to 8-membered cationic heterocycle optionally substituted with one or more radicals chosen from $C_1$-$C_4$ alkyl, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals; the said cationic radical being a linear or branched or cyclic, saturated or unsaturated radical, comprising a quaternary ammonium;

when $Z_1$ represents $NR_2$, then $R_1$ and $R_2$ may form, together with the nitrogen atom to which they are attached, a saturated or unsaturated 5- to 8-membered cationic heterocycle, at least one of the ring members of which is a quaternary ammonium, optionally substituted with one or more radicals chosen from $C_1$-$C_{10}$ alkyl, hydroxyl, $C_1$-$C_4$ alkoxy, amino, ($C_1$-$C_4$) alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals, this heterocycle possibly containing one or more heteroatoms chosen from N and O, preferably N, or $R_1$ and $R_2$ may form, together with the nitrogen atom to which they are attached, a saturated or unsaturated 5- to 8-membered non-cationic heterocycle, substituted with a cationic radical and optionally substituted with one or more radicals chosen from $C_1$-$C_{10}$ alkyl, hydroxyl, $C_1$-$C_4$ alkoxy, amino, ($C_1$-$C_4$)alkylamino, di($C_1$-$C_4$) alkylamino, thio, ($C_1$-$C_4$)alkylthio, carboxyl, ($C_1$-$C_4$) alkylcarbonyl, sulfonyl, amido and $C_1$-$C_4$ hydroxyalkyl radicals; the said cationic radical being a linear or branched or cyclic, saturated or unsaturated radical, comprising a quaternary ammonium;

R is chosen from a hydrogen atom, halogens chosen from fluorine, chlorine and bromine, and linear or branched $C_1$-$C_4$ alkyl, carboxyl (—COOH) and ($C_1$-$C_4$)alkoxycarbonyl radicals, An—represents an anion or a mixture of anions.

Preferably, the concentration of the cationic aminopyridine of general formula (I) is between 0.0001% and 20% and preferably between 0.005% and 6% by weight relative to the total weight of the composition.

The suitable dyeing medium generally comprises water or a mixture of water and of at least one organic solvent, for instance linear or branched $C_1$-$C_4$ lower alcohols, such as ethanol and isopropanol; polyols and polyol ethers, for instance 2-butoxyethanol, propylene glycol, propylene glycol monomethyl ether, diethylene glycol monomethyl ether and monoethyl ether, glycerol and also aromatic alcohols, for instance benzyl alcohol or phenoxyethanol, and mixtures thereof.

Advantageously, the cosmetic composition comprises at least one cosmetic adjuvant chosen from the group formed by antioxidants, penetrants, sequestrants, fragrances, buffers, dispersants, surfactants, conditioning agents, film-forming agents, polymers, ceramides, preserving agents, nacreous agents or opacifiers, and vitamins or provitamins.

The above adjuvants are generally present in an amount for each of them of between 0.01% and 20% by weight relative to the weight of the composition.

The composition also comprises at least one oxidation base. These bases may be chosen especially from para-phenylenediamines, bis(phenyl)alkylenediamines, para-aminophenols, ortho-aminophenols and heterocyclic bases, and the addition salts thereof.

Among the para-phenylenediamines, examples that may be mentioned more particularly include para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine and 6-(4-aminophenyl-amino) hexan-1-ol, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylene-diamine, 2-chloro-para-phenylenediamine and 2-β-acetylaminoethyloxy-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis-(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof with an acid.

Among the para-aminophenols, examples that may be mentioned include para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6[((5'-amino-2'-hydroxy-3'-methyl)phenyl)methyl]-2-methyl -phenol and bis[(5'-amino-2'-hydroxy)phenylmethane, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid.

Among the heterocyclic bases, examples that may be mentioned include pyridine derivatives, pyrimidine derivatives and pyrazole derivatives.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof with an acid.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyridin-3-ylamine; 2-acetylaminopyrazolo-[1,5-a]-pyridin-3-ylamine; 2-morpholin-4-ylpyrazolo[1,5-a]pyridin-3-ylamine; 3-aminopyrazolo[1,5-a]pyridine-2-carboxylic acid; 2-methoxypyrazolo[1,5-a]pyridin-3-ylamine; (3-aminopyrazolo yl)methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]-pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo-[1,5-a]pyridine-3,5-diamine; 5-morpholin-4-ylpyrazolo[1,5-a]pyridin-3-ylamine; 2-[(3-aminopyrazolo[1,5-a]pyridin-5-yl)(2-hydroxyethyl) -amino] ethanol; 2-[(3-aminopyrazolo[1,5-a]pyridin-7-yl)(2-hydroxyethyl) amino]ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol;

and also the addition salts thereof with an acid.

Among the pyrimidine derivatives, mention may be made of the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof and the tautomers thereof, when a tautomeric equilibrium exists.

Among the pyrazole derivatives that may be mentioned are the compounds described in patents DE 3 843 892, DE 4 133 957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof.

Generally, the concentration of the oxidation base(s) is between 0.0001% and 20% and preferably between 0.005% and 6% by weight relative to the total weight of the composition.

The composition according to the invention preferably contains at least one additional oxidation coupler, other than the cationic aminopyridines of general formula (I).

Among these oxidation couplers, mention may be made especially of meta-phenylenediamines, meta-aminophenols, meta-diphenols, naphthalene-based couplers and heterocyclic couplers, and also the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis-(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino) toluene, and the addition salts thereof.

Generally, the concentration of the oxidation coupler(s) is between 0.0001% and 20% and preferably between 0.005% and 6% by weight relative to the total weight of the composition.

In general, the addition salts with an acid that may be used for the oxidation bases and couplers are chosen especially from the hydrochlorides, hydrobromides, sulfates, citrates, succinates, tartrates, lactates, tosylates, benzenesulfonates, phosphates and acetates.

The dye composition in accordance with the invention may also contain one or more direct dyes, which may be chosen especially from neutral, acidic or cationic nitrobenzene dyes, neutral, acidic or cationic azo direct dyes, neutral, acidic or cationic quinone and in particular anthraquinone direct dyes, azine direct dyes, methine, azomethine, triarylmethane or indoamine direct dyes and natural direct dyes. Preferably, the composition according to the invention comprises at least one dye chosen from cationic direct dyes and natural direct dyes.

Among the cationic direct dyes that may be used according to the invention, mention may be made of the cationic azo direct dyes described in patent applications WO 95/15144, WO-95/01772 and EP-714 954.

Among these compounds, mention may be made most particularly of the following dyes:
- 1,3-dimethyl-2-[[4-(dimethylamino)phenyl]azo]-1H-imidazolium chloride,
- 1,3-dimethyl-2-[(4-aminophenyl)azo]-1H-imidazolium chloride,
- 1-methyl-4-[(methylphenylhydrazono)methyl]pyridinium methyl sulfate.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and especially henna-based poultices or extracts may also be used.

The direct dye(s) preferably represent from 0.001% to 20% by weight approximately and even more preferentially from 0.005% to 10% by weight approximately relative to the total weight of the composition.

Needless to say, a person skilled in the art will take care to select the adjuvant(s), additional oxidation dye precursors and direct dyes such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents usually used in the dyeing of keratin fibres, or alternatively using standard buffer systems.

Among the acidifying agents, examples that may be mentioned include mineral or organic acids other than carboxylic acids, for instance hydrochloric acid, orthophosphoric acid, sulfuric acid, carboxylic acids such as acetic acid, tartaric acid, citric acid and lactic acid, and sulfonic acids.

Among the basifying agents, examples that may be mentioned include aqueous ammonia, alkali metal carbonates, alkanolamines such as monoethanolamine, diethanolamine and triethanolamine, and also derivatives thereof, sodium hydroxide, potassium hydroxide and the compounds of formula:

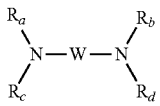

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical.

The cosmetic composition according to the invention may be in various forms, such as in the form of liquids, creams or gels, or in any other form that is suitable for dyeing keratin fibres, and especially human hair.

The present patent application relates to a process in which the composition according to the present invention as defined previously is applied to keratin fibres for a time sufficient to develop the desired colouring in the presence of an oxidizing agent, the oxidizing agent being applied before, simultaneously with or after the composition.

The colour may be revealed at acidic, neutral or alkaline pH and the oxidizing agent may be added to the composition of the invention just before the time of use, or it may be used starting with an oxidizing composition containing it, which is applied simultaneously with or sequentially to the composition of the invention.

According to one particular embodiment, the composition according to the present invention is mixed, preferably at the time of use, with a composition containing, in a suitable dyeing medium, at least one oxidizing agent, this oxidizing agent being present in an amount sufficient to develop a coloration.

According to this particular embodiment, a ready-to-use composition is provided, which is a mixture of a composition according to the invention with an oxidizing composition comprising at least one oxidizing agent preferably chosen from hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred. The mixture obtained is then applied to the keratin fibres for a time sufficient to develop the desired coloration. After a leave-on time of 3 to 50 minutes approximately and preferably 5 to 30 minutes approximately, the keratin fibres are rinsed, washed with shampoo, rinsed again and then dried.

The oxidizing composition may also contain various adjuvants conventionally used in hair dye compositions and as defined previously.

The pH of the oxidizing composition containing the oxidizing agent is such that after mixing with the dye composition, the pH of the resulting composition applied to the keratin fibres preferably ranges between 3 and 12 approximately and even more preferentially between 5 and 11. It may be adjusted to the desired value by means of acidifying or basifying agents usually used in the dyeing of keratin fibres and as defined previously.

The ready-to-use composition that is finally applied to the keratin fibres may be in various forms, such as in the form of liquids, creams or gels, or in any other form that is suitable for dyeing keratin fibres, and especially human hair.

A subject of the present patent application is also a process for dyeing keratin fibres, in which the ready-to-use composition is applied to the said fibres for a time sufficient to develop the desired coloration.

The time sufficient to develop the desired coloration generally corresponds to a leave-on time of 3 to 50 minutes approximately and preferably 5 to 30 minutes approximately.

A subject of the invention is also a multi-compartment dyeing device or "kit" in which a first compartment contains the dye composition defined above and a second compartment contains an oxidizing agent. This device may be equipped with a means for dispensing the desired mixture on the hair, such as the devices described in patent FR-2 586 913 in the name of the Applicant.

Using this device, it is possible to dye keratin fibres by means of a process that includes the mixing of a dye composition in accordance with the invention with an oxidizing agent as defined previously, and the application of the mixture obtained onto the keratin fibres for a time sufficient to develop the desired coloration.

The examples that follow serve to illustrate the invention without, however, being limiting in nature.

EXAMPLES

Examples of Synthesis

Example 1

Synthesis of 2-[(3,5-diaminopyridin-2-yl)amino]-N,N,N-trimethylethaneammonium chloride dihydrochloride (compound 1)

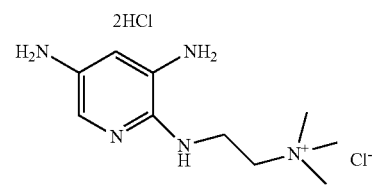

Synthesis of N'-(3,5-dinitropyridin-2-yl)-N,N-dimethylethane-1,2-diamine

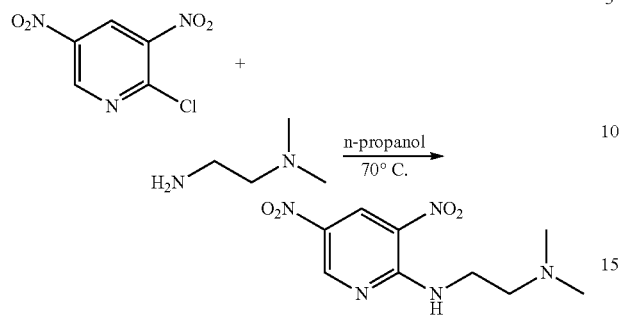

30 ml of ethanol and 10.15 g (0.05 mol) of 2-chloro-3,5-dinitropyridine are successively placed in a 50 ml three-necked round-bottomed flask equipped with a thermometer, a condenser, a bubbler and a dropping funnel, with magnetic stirring. The medium is brought to 40° C., 8.8 g (0.1 mol) of N,N-dimethylethane-1,2-diamine are added dropwise via the dropping funnel over 5 minutes, and the mixture is stirred for 1 hour.

After cooling the reaction medium, it is poured into a mixture of ice and water with stirring.

The yellow solid formed is isolated by filtration on a sinter funnel, washed with water and dried under vacuum at 30° C. in the presence of a drying agent, to constant weight. 10.5 g (yield of 82.5%) of expected compound are thus obtained in the form of a yellow solid.

Analysis by mass spectrometry confirms the expected compound: The quasi-molecular ions $[M+H]^+$ and $[M+Na]^+$ of the expected molecule $C_9H_{13}N_5O_4$ are mainly detected.

2-[(3,5-dinitropyridin-2-yl)amino]-N,N,N-trimethylethaneammonium methyl sulfate

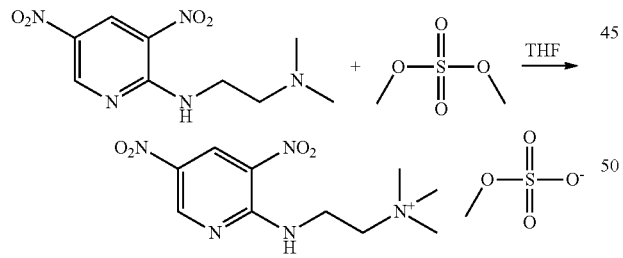

50 ml of ethyl acetate and 6.38 g (25 mmol) of N'-(3,5-dinitropyridin-2-yl)-N,N-dimethylethane-1,2-diamine are successively placed in a 100 ml three-necked round-bottomed flask equipped with a thermometer, a condenser, a bubbler and a dropping funnel, with magnetic stirring. 3.15 g (25 mmol) of dimethyl sulfate are then poured into this solution, and the mixture is stirred for one hour.

The yellow solid formed is filtered off, dried by suction, washed with ethyl acetate and then dried under vacuum at 50° C. in the presence of a drying agent, to constant mass. 7 g (73% yield) of expected compound are thus obtained in the form of a yellow solid.

Analysis by mass spectrometry confirms the expected compound; the expected cation $[C_{10}H_{16}N_5O_4]^+$ is mainly detected at m/z, $ESP^+=270$.

Synthesis of 2-[(3,5-diaminopyridin-2-yl)amino]-N,N,N-trimethylethaneammonium chloride dihydrochloride

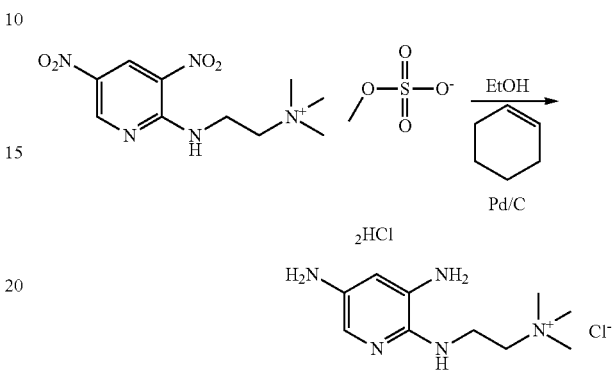

300 ml of ethanol, 20 ml of water, 24 g (62.95 mmol) of 2-[(3,5-dinitropyridin-2-yl)amino]-N,N,N-trimethylethaneammonium methyl sulfate and 52 ml (503 mmol) of cyclohexene are successively placed in a 1 L three-necked round-bottomed flask equipped with a thermometer, a condenser and a bubbler, with magnetic stirring. The medium is brought to 50° C., 12 g of palladium-on-charcoal are added portionwise and the mixture is refluxed for 2 hours.

After cooling under argon, the reaction medium is filtered under a stream of argon on a sinter funnel packed with Celite and over a vacuum flask containing 200 ml of 6.0 N hydrochloric 2-propanol at 0° C.

The expected compound crystallizes in the vacuum flask with stirring. The solid is filtered off, dried quickly by suction on a sinter funnel under argon, and rinsed with a minimum amount of cold iPrOH and then with 3×100 ml of $iPr_2O$. The compound is dried under vacuum at 50° C. in the presence of a drying agent, to constant weight. 17.5 g (87.4% yield) of expected compound are thus obtained in the form of a beige-coloured solid.

The analyses by NMR ($^1H$ 400 MHz and $^{13}C$ 100.61 MHz DMSO-$d_6$) and mass spectrometry are in accordance with the expected structure.

Example 2

Synthesis of 2-[(3,5-diaminopyridin-2-yl)(methyl)-amino]-N,N,N-trimethylethaneammonium chloride dihydrochloride

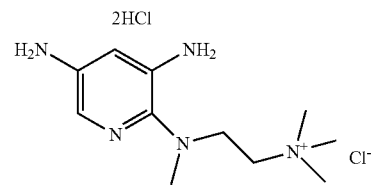 [SMILES: CN(CC[N+](C)(C)C)c1ncc(N)cc1N ; [Cl-]]

Synthesis of N-(3,5-dinitropyridin-2-yl)-N,N',N'-trimethylethane-1,2-diamine

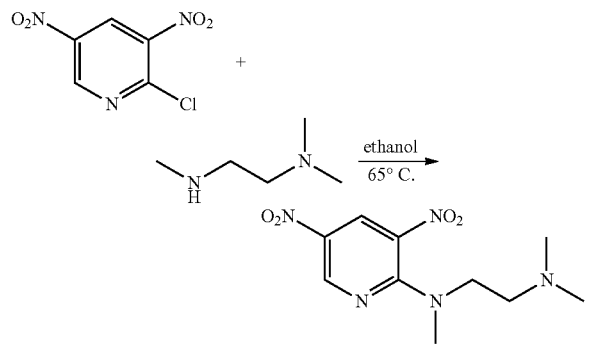

50 ml of ethanol and 12.30 g (60.43 mmol) of 2-chloro-3,5-dinitropyridine are successively placed in a 250 ml three-necked round-bottomed flask equipped with a thermometer, a condenser, a bubbler and a dropping funnel, with magnetic stirring. The medium is brought to 40° C., 9.26 ml (72.52 mmol) of N,N,N'-trimethylethane-1,2-diamine are added dropwise via the dropping funnel, over 5 minutes, and the mixture is maintained at 65° C. for 1 hour.

After cooling the reaction medium, it is poured into a mixture of 200 g of ice and water, with stirring.

The yellow solid formed is isolated by filtration on a sinter funnel, washed with water and dried under vacuum at 30° C. in the presence of a drying agent, to constant weight. 10.7 g (yield of 62%) of yellow solid corresponding to the expected compound are thus isolated.

Analysis by mass spectrometry confirms the expected compound: The quasi-molecular ions $[M+H]^+$ and $[M+Na]^+$ of the expected molecule $C_{10}H_{15}N_5O_4$ are mainly detected.

2-[(3,5-dinitropyridin-2-yl)(methyl)amino]-N,N,N-trimethylethaneammonium methyl sulfate

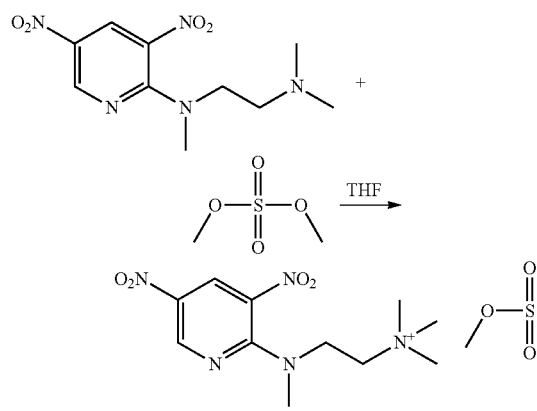

300 ml of ethyl acetate and 15.80 g (60 mmol) of N-(3,5-dinitropyridin-2-yl)-N,N',N'-trimethylethane-1,2-diamine are successively placed in a 500 ml three-necked round-bottomed flask equipped with a thermometer, a condenser, a bubbler and a dropping funnel, with magnetic stirring.

12 g (120 mmol) of dimethyl sulfate are added dropwise to this solution, and the mixture is stirred at reflux for one hour.

After cooling, the yellow solid formed is filtered off on a sinter funnel, dried by suction, washed with ethyl acetate and then dried under vacuum at 50° C. in the presence of a drying agent, to constant mass. 22.3 g (94% yield) of expected compound are thus isolated in the form of a yellow solid.

Analysis by mass spectrometry confirms the expected compound; the expected cation $[C_{11}H_{18}N_5O_4]^+$ is mainly detected at m/z, $ESP^+=284$.

Synthesis of 2-[(3,5-diaminopyridin-2-yl)(methyl)amino]-N,N,N-trimethylethaneammonium chloride dihydrochloride

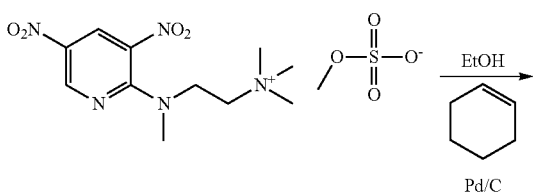

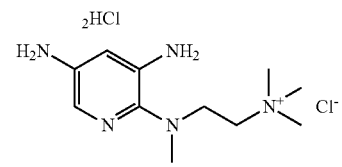

300 ml of ethanol, 5 ml of water, 20 g (50.60 mmol) of 2-[(3,5-dinitropyridin-2-yl)amino]-N,N,N-trimethylethaneammonium methyl sulfate and 104 ml of cyclohexene are successively placed in a 1 L three-necked round-bottomed flask equipped with a thermometer, a condenser and a bubbler, with magnetic stirring.

The medium is brought to 50° C., 5 g of palladium-on-charcoal are added portionwise, and the mixture is refluxed for 2 hours.

After cooling under argon, the reaction medium is filtered under a stream of argon on a sinter funnel packed with Celite and over a vacuum flask containing 250 ml of 6.0 N hydrochloric 2-propanol at 0° C.

The expected compound, which crystallizes in the flask with stirring, is filtered off, dried rapidly by suction on a sinter funnel under argon, and rinsed with a minimum amount of cold iPrOH and then with 3×100 ml of $iPr_2O$. The compound is dried under vacuum at 50° C. in the presence of a drying agent, to constant weight. 12.1 g (81% yield) of expected compound are thus isolated in the form of a beige-coloured solid.

The analyses by NMR ($^1$H 400 MHz and $^{13}$C 100.61 MHz DMSO-d$_6$) and mass spectrometry are in accordance with the expected structure.

Example 3

Synthesis of 4-(3,5-diaminopyridin-2-yl)-1,1-dimethylpiperazin-1-ium chloride dihydrochloride

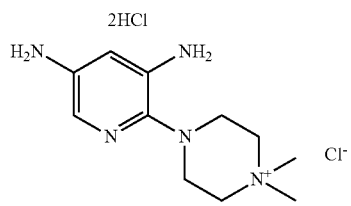

Synthesis of 1-(3,5-dinitropyridin-2-yl)-4-methylpiperazine

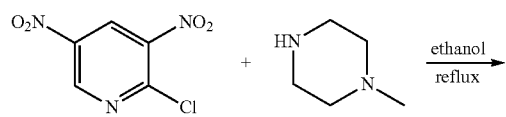

40 ml of ethanol and 5 g (24.57 mmol) of 2-chloro-3,5-dinitropyridine are successively placed in a 250 ml three-necked round-bottomed flask equipped with a thermometer, a condenser, a bubbler and a dropping funnel, with magnetic stirring. The medium is brought to 40° C., 6.15 ml (49.13 mmol) of methylpiperazine are added dropwise via the dropping funnel, over 5 minutes, and the mixture is refluxed for 1 hour and then stirred at room temperature overnight.

A yellow solid crystallizes from the medium. It is isolated by filtration on a sinter funnel, washed with water and dried under vacuum at 30° C. in the presence of a drying agent, to constant weight. 5.7 g (yield of 88%) of expected compound are thus isolated in the form of a yellow solid.

Analysis by mass spectrometry confirms the structure of the expected compound: The quasi-molecular ions [M+H]$^+$ and [M+Na]$^+$ of the expected molecule C$_{10}$H$_{13}$N$_5$O$_4$ are mainly detected.

Synthesis of 4-(3,5-dinitropyridin-2-yl)-1,1-dimethylpiperazin-1-ium methyl sulfate

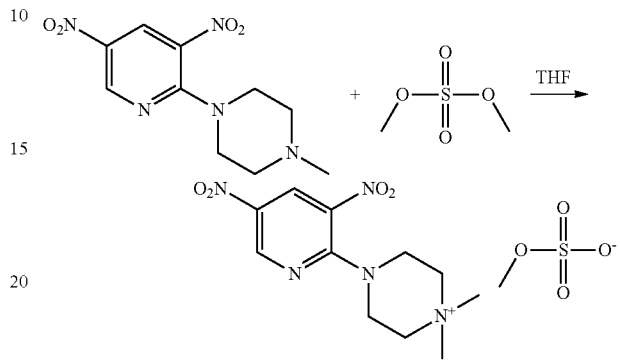

100 ml of THF and 5.5 g (20 mmol) of 1-(3,5-dinitropyridin-2-yl)-4-methylpiperazine are successively placed in a 200 ml three-necked round-bottomed flask equipped with a thermometer, a condenser, a bubbler and a dropping funnel, with magnetic stirring.

4.19 g (40 mmol) of dimethyl sulfate are added dropwise to this solution, and the mixture is stirred at reflux for one hour.

The yellow solid formed is filtered off on a sinter funnel, dried by suction, washed with THF and then dried under vacuum at 50° C. in the presence of a drying agent, to constant mass. 7.4 g (yield 94%) of expected compound are thus isolated in the form of a yellow solid.

Analysis by mass spectrometry confirms the structure of the expected compound. The expected cation [C$_{15}$H$_{16}$N$_5$O$_4$]$^+$ is mainly detected.

Synthesis of 4-(3,5-diaminopyridin-2-yl)-1,1-dimethylpiperazin-1-ium chloride hydrochloride

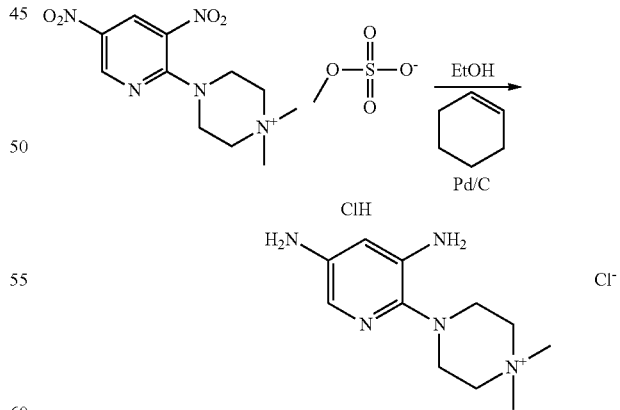

50 ml of ethanol, 1 ml of water, 20 g (50.60 mmol) of 4-(3,5-dinitropyridin-2-yl)-1,1-dimethylpiperazin-1-ium methyl sulfate and 36.56 ml of cyclohexene are successively placed in a 250 ml three-necked round-bottomed flask equipped with a thermometer, a condenser and a bubbler, with magnetic stirring.

The medium is brought to 50° C., 3.5 g of palladium-on-charcoal are added portionwise, and the mixture is then refluxed for 24 hours.

The reaction medium is filtered under argon on a sinter funnel packed with Celite and over a vacuum flask containing 250 ml of 6.0 N hydrochloric 2-propanol at 0° C.

The expected compound crystallizes in the flask with stirring; it is filtered off on a sinter funnel, dried rapidly by suction under argon, and rinsed with a minimum amount of cold iPrOH and then with 3×100 ml of iPr$_2$O. The solid is then dried under vacuum at 50° C. in the presence of a drying agent, to constant weight. 4.6 g (88% yield) of expected compound are thus isolated in the form of a beige-coloured solid.

The analyses by NMR ($^1$H 400 MHz and $^{13}$C 100.61 MHz DMSO-d$_6$) and mass spectrometry are in accordance with the expected structure.

The expected cation [C$_{11}$H$_{20}$N$_5$] is mainly detected

Example 4

Synthesis of 1-{2-[(3,5-diaminopyridin-2-yl)-amino]ethyl}-1-methylpiperidinium chloride dihydrochloride

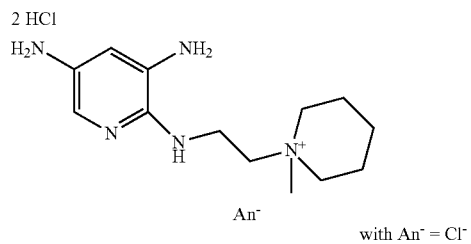 [SMILES: C[N+]1(CCNc2ncc(N)cc2N)CCCCC1]

Synthesis of 3,5-dinitro-N-(2-piperidin-1-ylethyl)pyridine-2-amine

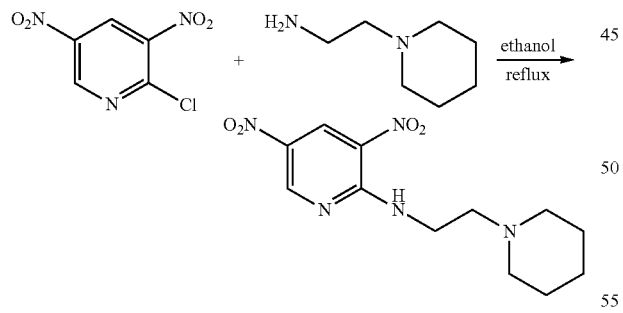

800 ml of ethanol and 10.17 g (50 mmol) of 2-chloro-3,5-dinitropyridine are successively placed in a 250 ml three-necked round-bottomed flask equipped with a thermometer, a condenser, a bubbler and a dropping funnel, with magnetic stirring. This medium is brought to 40° C., 7 ml of 2-aminoethylpiperidine are added dropwise via the dropping funnel, over 5 minutes, and the mixture is then stirred for one hour.

The medium, which has become heterogeneous, is then poured onto 500 g of ice. A yellow solid precipitates more abundantly; it is isolated by filtration on a sinter funnel, washed with water and dried under vacuum at 30° C. in the presence of a drying agent, to constant weight. 11.5 g (78% yield) of expected compound are thus isolated in the form of a yellow solid.

Analysis by mass spectrometry confirms the structure of the expected compound: the quasi-molecular ions [M+H]$^+$ and [M+Na]$^+$ of the expected molecule C$_{12}$H$_{17}$N$_5$O$_4$ are mainly detected.

Synthesis of 1-{2-[(3,5-dinitropyridin-2-yl)amino]ethyl}-1-methylpiperidinium methyl sulfate

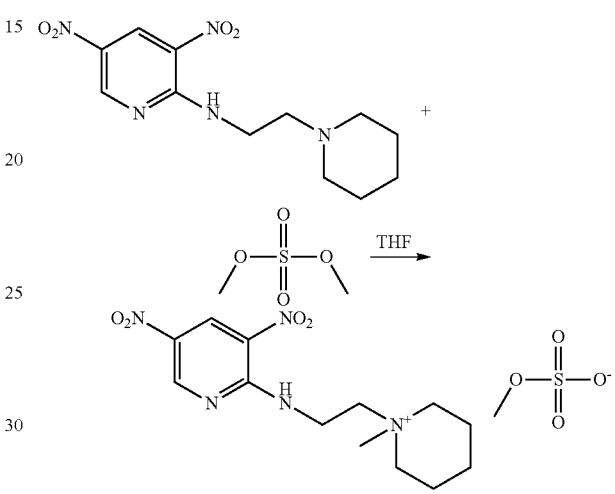

50 ml of ethyl acetate and 6.16 g (20 mmol) of 3,5-dinitro-N-(2-piperidin-1-ylethyl)pyridine-2-amine are successively placed in a 200 ml three-necked round-bottomed flask equipped with a thermometer, a condenser, a bubbler and a dropping funnel, with magnetic stirring.

2.52 g (20 mmol) of dimethyl sulfate are added dropwise and the mixture is stirred for one hour.

The yellow solid formed is filtered off on a sinter funnel, dried by suction, washed with ethyl acetate and then dried under vacuum at 50° C. in the presence of a drying agent, to constant mass. 7.6 g (90% yield) of expected compound are thus isolated in the form of a yellow solid.

Analysis by mass spectrometry confirms the structure of the expected compound. The expected cation [C$_{13}$H$_{20}$N$_5$O$_4$]$^+$ is mainly detected.

Synthesis of 1-{2-[(3,5-diaminopyridin-2-yl)amino]ethyl}-1-methylpiperidinium chloride dihydrochloride

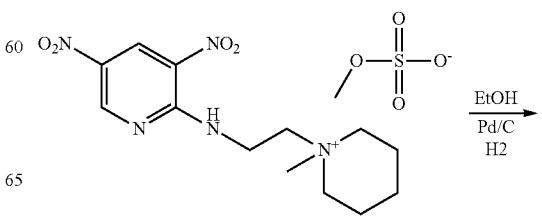

-continued

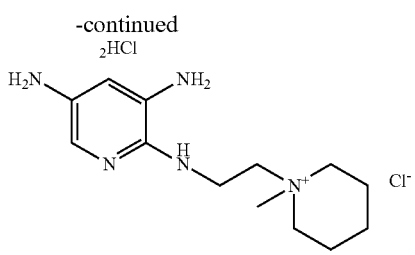

150 ml of ethanol, 5 ml of water, 6 g (14.2 mmol) of 1-{2-[(3,5-dinitropyridin-2-yl)amino]ethyl}-1-methylpiperidinium methyl sulfate and 1.2 g of palladium-on-charcoal are successively placed in a 300 ml hydrogenation autoclave.

After purging the medium with nitrogen and then with hydrogen, the reaction is performed under a hydrogen pressure of 8 bar with an exothermicity of 75° C.

After cooling and purging with hydrogen, the catalyst is removed under nitrogen and the liquors are poured under nitrogen into 100 ml of 6N hydrochloric isopropanol.

The beige-coloured solid that crystallizes slowly under cold conditions is dried rapidly by suction on a sinter funnel under argon, and rinsed with a minimum amount of cold iPrOH and then with 3×100 ml of iPr$_2$O. The solid obtained is dried under vacuum at 50° C. in the presence of a drying agent, to constant weight. 4.8 g (94% yield) of expected compound are thus isolated in the form of a beige-coloured solid.

The analyses by NMR ($^1$H 400 MHz and $^{13}$C 100.61 MHz DMSO-d$_6$) and mass spectrometry are in accordance with the expected structure.

The expected cation $[C_{13}H_{24}N_5]^+$ is mainly detected

Example 5

Synthesis of 1-(3,5-diaminopyridin-2-yl)-N,N,N-trimethylpyrrolidine-3-ammonium chloride hydrochloride The procedure is identical to that described in Example 4, the amine being N-dimethylpyrrolidine-3-amine.

The beige-coloured 1-(3,5-diaminopyridin-2-yl)-N,N,N-trimethylpyrrolidine-3-ammonium chloride hydrochloride is obtained in a yield of 65%.

The analyses by NMR ($^1$H 400 MHz and $^{13}$C 100.61 MHz DMSO-d$_6$) and mass spectrometry are in accordance with the expected structure.

The expected cation $[C_{12}H_{22}N_5]^+$ is mainly detected.

Example 6

Synthesis of 1-{3-[(3,5-diaminopyridin-2-yl)-amino]propyl}-3-(2-hydroxyethyl)-1H-imidazol-3-ium chloride dihydrochloride

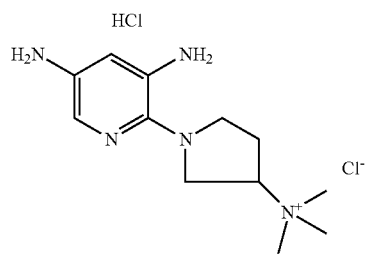 [SMILES: Cl ; C[N+](C)(C)C1CCN(c2ncc(N)cc2N)C1 ; [Cl-]]

The process is performed in an identical manner to that of Example 4, with substitution using 3-aminopropylimidazole and cationization using chloroethanol, followed by a catalytic reduction in an autoclave.

The analyses by NMR ($^1$H 400 MHz and $^{13}$C 100.61 MHz DMSO-d$_6$) and mass spectrometry are in accordance with the expected structure.

The expected cation $[C_{13}H_{21}N_5O]^+$ is mainly detected.

Examples of Dyeing

The following dye compositions are prepared:

| Examples | 1 | 2 | 3 | 4 |
|---|---|---|---|---|
| 2-[(3,5-diaminopyridin-2-yl)amino]-N,N,N-trimethylethaneammonium chloride dihydrochloride | $10^{-3}$ mol | $10^{-3}$ mol | $10^{-3}$ mol | $10^{-3}$ mol |
| 2,3-diamino-6,7-dihydro-1H,5H-pyrazolo[1,2-a]pyrazol-1-one dimethanesulfonate | $10^{-3}$ mol | — | — | — |
| 2-[(3-aminopyrazolo[1,5-a]pyridin-2-yl)oxy]ethanol hydrochloride | — | $10^{-3}$ mol | — | — |

-continued

| | | | | |
|---|---|---|---|---|
| 4-(3-aminopyrazolo[1,5-a]pyridin-2-yl)-1,1-dimethylpiperazin-1-ium chloride hydrochloride | — | — | $10^{-3}$ mol | — |
| 1-{2-[(3-aminopyrazolo[1,5-a]pyridin-2-yl)amino]ethyl}-3-methyl-1H-imidazol-3-ium chloride dihydrochloride | — | — | — | $10^{-3}$ mol |
| Dye support (1) | (*) | (*) | (*) | (*) |
| Demineralized water qs | 100 g | 100 g | 100 g | 100 g |
| Shade observed | strong chromatic red | strong grey | strong green | strong green |

| Examples | 5 | 6 | 7 | 8 |
|---|---|---|---|---|
| 2-[(3,5-diaminopyridin-2-yl)amino]-N,N,N-trimethylethaneammonium chloride dihydrochloride | $10^{-3}$ mol | $10^{-3}$ mol | $10^{-3}$ mol | $10^{-3}$ mol |
| 2,3-diamino-6,7-dihydro-1H,5H-pyrazolo[1,2-a]pyrazol-1-one dimethanesulfonate | $10^{-3}$ mol | — | — | — |
| 2-[(3-aminopyrazolo[1,5-a]pyridin-2-yl)oxy]-ethanol hydrochloride | — | $10^{-3}$ mol | — | — |
| 4-(3-aminopyrazolo[1,5-a]pyridin-2-yl)-1,1-dimethylpiperazin-1-ium chloride hydrochloride | — | — | $10^{-3}$ mol | — |
| 1-{2-[(3-aminopyrazolo-[1,5-a]pyridin-2-yl)amino]-ethyl}-3-methyl-1H-imidazol-3-ium chloride dihydrochloride | — | — | — | $10^{-3}$ mol |
| Dye support (1) | (*) | (*) | (*) | (*) |
| Demineralized water qs | 100 g | 100 g | 100 g | 100 g |
| Shade observed | strong red | strong brown-grey | strong green-grey | strong green |

| Examples | 9 | 10 | 11 | 12 |
|---|---|---|---|---|
| 4-(3,5-diaminopyridin-2-yl)-1,1-dimethyl-piperazin-1-ium chloride hydrochloride | $10^{-3}$ mol | $10^{-3}$ mol | $10^{-3}$ mol | $10^{-3}$ mol |
| 2,3-diamino-6,7-dihydro-1H,5H-pyrazolo[1,2-a]pyrazol-1-one dimethanesulfonate | $10^{-3}$ mol | — | — | — |
| 2-[(3-aminopyrazolo[1,5-a]pyridin-2-yl)oxy]ethanol hydrochloride | — | $10^{-3}$ mol | — | — |
| 4-(3-aminopyrazolo[1,5-a]pyridin-2-yl)-1,1-dimethylpiperazin-1-ium chloride hydrochloride | — | — | $10^{-3}$ mol | — |
| 1-{2-[(3-aminopyrazolo[1,5-a]pyridin-2-yl)amino]ethyl}-3-methyl-1H-imidazol-3-ium chloride dihydrochloride | — | — | — | $10^{-3}$ mol |
| Dye support (1) | (*) | (*) | (*) | (*) |
| Demineralized water qs | 100 g | 100 g | 100 g | 100 g |
| Shade observed | strong chromatic red | strong chromatic red-brown | strong green-grey | strong chromatic green |

| Examples | 13 | 14 | 15 | 16 |
|---|---|---|---|---|
| 1{2-[(3,5-diaminopyridin-2-yl)amino]ethyl}-1-methylpiperidinium chloride dihydrochloride | $10^{-3}$ mol | $10^{-3}$ mol | $10^{-3}$ mol | $10^{-3}$ mol |
| 2,3-diamino-6,7-dihydro-1H,5H-pyrazolo[1,2-a]-pyrazol-1-one dimethanesulfonate | $10^{-3}$ mol | | | |

-continued

| | | | | |
|---|---|---|---|---|
| 2-[(3-aminopyrazolo-[1,5-a]pyridin-2-yl)oxy]-ethanol hydrochloride | — | $10^{-3}$ mol | — | — |
| 4-(3-aminopyrazolo[1,5-a]pyridin-2-yl)-1,1-dimethylpiperazin-1-ium chloride hydrochloride | — | — | $10^{-3}$ mol | — |
| 1-{2-[(3-aminopyrazolo[1,5-a]pyridin-2-yl)amino]ethyl}-3-methyl-1H-imidazol-3-ium chloride dihydrochloride | — | — | — | $10^{-3}$ mol |
| Dye support (1) | (*) | (*) | (*) | (*) |
| Demineralized water qs | 100 g | 100 g | 100 g | 100 g |
| Shade observed | strong chromatic red | strong chromatic red-brown | strong green-grey | strong chromatic green |

(*) dye support (1) pH 9.5

| | |
|---|---|
| 96° ethanol | 20.8 g |
| Sodium metabisulfite as an aqueous solution at 35% by weight | 0.23 g AM |
| Pentasodium salt of diethylenetriaminepentaacetic acid as an aqueous solution at 40% by weight | 0.48 g AM |
| $C_8$-$C_{10}$ alkyl polyglucoside as an aqueous solution at 60% by weight | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% by weight of $NH_3$ in water | 2.94 g |

AM: active material

At the time of use, each composition is mixed with an equal weight of 20-volumes aqueous hydrogen peroxide solution (6% by weight). A final pH of 9.5 is obtained.

Each mixture obtained is applied to locks of grey hair containing 90% white hairs. After a leave-on time of 30 minutes, the locks are rinsed, washed with a standard shampoo, rinsed again and then dried to give the shades mentioned.

The invention claimed is:
1. Cationic aminopyridine chosen from:
the compounds of general formula (I'), acid-addition salts thereof and solvates thereof:

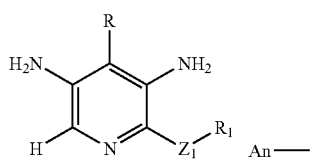

(I')

in which the group $Z_1R_1$ is cationic,
$Z_1$ is an oxygen atom or a group $NR_2$;
$R_2$ is a hydrogen atom or a linear or branched $C_1$-$C_4$ alkyl radical, a benzyl radical or an acetyl radical;
$R_1$ is a linear or branched saturated $C_1$-$C_{10}$ alkyl radical, substituted or interrupted with a cationic radical, optionally interrupted with one or more oxygen atoms and/or with one or more groups $NR_2$, optionally substituted with one or more radicals chosen from hydroxyl and $C_1$-$C_4$ alkoxy or hydroxyalkyl radicals, the said cationic radical being a linear, branched or cyclic, saturated or unsaturated radical, comprising a quaternary ammonium; or $R_1$ is a saturated, unsaturated or aromatic, 5- to 8-membered cationic heterocycle optionally substituted with one or more radicals chosen from $C_1$-$C_4$ alkyl, hydroxyl, $C_1$-$C_4$ alkoxy, amino, $(C_1$-$C_4)$alkylamino, di$(C_1$-$C_4)$alkylamino, thio, $(C_1$-$C_4)$alkylthio, carboxyl, $(C_1$-$C_4)$alkylcarbonyl, sulfonyl, amido and $C_1$-$C_4$ hydroxyalkyl radicals;

when $Z_1$ represents $NR_2$, then
$R_1$ and $R_2$ may form, together with the nitrogen atom to which they are attached, an unsaturated 5- to 8-membered cationic heterocycle, optionally substituted with one or more radicals chosen from $C_1$-$C_{10}$ alkyl, hydroxyl, $C_1$-$C_4$ alkoxy, amino, $(C_1$-$C_4)$alkylamino, di$(C_1$-$C_4)$alkylamino, thio, $(C_1$-$C_4)$alkylthio, carboxyl, $(C_1$-$C_4)$alkylcarbonyl, sulfonyl, amido and $C_1$-$C_4$ hydroxyalkyl radicals, this heterocycle possibly containing one or more heteroatoms chosen from N and O, or
$R_1$ and $R_2$ may form, together with the nitrogen atom to which they are attached, an unsaturated 5- to 8-membered non-cationic heterocycle, substituted with a cationic radical and optionally substituted with one or more radicals chosen from $C_1$-$C_{10}$ alkyl, hydroxyl, $C_1$-$C_4$ alkoxy, amino, $(C_1$-$C_4)$alkylamino, di$(C_1$-$C_4)$alkylamino, thio, $(C_1$-$C_4)$alkylthio, carboxyl, $(C_1$-$C_4)$alkylcarbonyl, sulfonyl, amido and $C_1$-$C_4$ hydroxyalkyl radicals; the said cationic radical being a linear, branched or cyclic, saturated or unsaturated radical, comprising a quaternary ammonium;
R is chosen from a hydrogen atom, halogens chosen from fluorine, chlorine and bromine, and linear or branched $C_1$-$C_4$ alkyl, carboxyl (—COOH) and $(C_1$-$C_4)$alkoxycarbonyl radicals,
An— represents an anion or a mixture of anions,
the following compounds, acid-addition salts thereof and solvates thereof:
1-(3,5-diaminopyridin-2-yl)-N,N,N-trimethylpyrrolidine-3-ammonium, 4-(3,5-diaminopyridin-2-yl)-1-(2-hydroxyethyl)-1-methylpiperazin-1-ium,
4-(3,5-diaminopyridin-2-yl)-1,1-bis(2-hydroxyethyl)piperazin-1-ium,
4-(3,5-diaminopyridin-2-yl)(2-trimethylethane)morpholineammonium,
4-(3,5-diaminopyridin-2-yl)(2-trimethylmethane)morpholineammonium,
4-(3,5-diaminopyridin-2-yl)(2-methyldiethylethane)morpholineammonium,
4-(3,5-diaminopyridin-2-yl)(2-methyldiethylmethan) morpholineammonium,
4-(3,5-diaminopyridin-2-yl)morpholine}-2-1,1-dimethylpyrrolidinium, (3,5-diaminopyridin-2-yl)-3-trimethylpiperidineammonium, (3,5-diaminopyridin-2-yl)-4-trimethylpiperidineammonium.

2. Cationic aminopyridine according to claim 1, in which the cationic radical is an N,N-dimethylpiperazinium or a linear or branched or cyclic, saturated or unsaturated radical, comprising a quaternary ammonium, this quaternary ammonium being of the type —N⁺RaRbRc, Ra, Rb and Rc, which may be identical or different, representing a $C_1$-$C_6$ alkyl radical that may be substituted with a hydroxyl, Ra and Rb, possibly forming, together with the nitrogen atom to which they are attached, a saturated or unsaturated 5- to 8-membered cationic heterocycle, the radical Rc, when it is present, then being a $C_1$-$C_6$ alkyl radical that may be substituted with a hydroxyl.

3. Cationic aminopyridine according to claim 2, in which the quaternary ammonium is chosen from trimethylammonium, triethylammonium, dimethylethylammonium, diethylmethylammonium, diisopropylmethylammonium, diethylpropylammonium, hydroxyethyldiethylammonium, di-β-hydroxyethylmethylammonium, tri-β-hydroxyethylammonium, N-methylpiperidinium, N-methylpyrrolidinium, N-methylmorpholinium, imidazolium, hydroxyethylimidazolium, methylimidazolium and N-methylpiperazinium radicals.

4. Cationic aminopyridine according to claim 1, in which $R_1$ is a $C_1$-$C_8$ alkyl radical substituted or interrupted with a cationic radical as defined in any one of the preceding claims, optionally interrupted with one or more oxygen atoms and/or with one or more groups $NR_2$, optionally substituted with a hydroxyl radical.

5. Cationic aminopyridine according to claim 1, in which $Z_1$ is an oxygen atom or $NR_2$ with $R_2$ chosen from hydrogen and a linear or branched $C_1$-$C_4$ alkyl radical, and $R_1$ represents a saturated linear $C_2$-$C_8$ alkyl radical, optionally interrupted with an oxygen atom or with a group NH, optionally substituted with a hydroxyl radical, and substituted or interrupted with a cationic radical chosen from trimethylammonium and imidazolium radicals.

6. Cationic aminopyridine according to claim 1, in which $Z_1$ is a group $NR_2$ and $R_1$ and $R_2$ form, together with the nitrogen atom to which they are attached, an unsaturated 5- to 8-membered cationic heterocycle, optionally substituted with one or more radicals chosen from $C_1$-$C_{10}$ alkyl and $C_1$-$C_{10}$ hydroxyalkyl radicals.

7. Cationic aminopyridine according to claim 1, in which $Z_1$ is a group $NR_2$ and $R_1$ and $R_2$ form, together with the nitrogen atom to which they are attached, an unsaturated 5- to 8-membered non-cationic heterocycle, substituted with a cationic radical as defined in any one of the preceding claims.

8. Cationic aminopyridine according to claim 1 is chosen from the following compounds: 2-[(3,5-diaminopyridin-2-yl)amino]-N,N,N-trimethylethaneammonium, 2-[(3,5-diaminopyridin-2-yl)(methyl)amino]-N,N,N-trimethylethaneammonium, 1-{2-[(3,5-diaminopyridin-2-yl)amino]ethyl}-1-methylpiperidinium, 1-(3,5-diaminopyridin-2-yl)-N,N,N-trimethylpyrrolidine-3-ammonium, 1-{3-[(3,5-diaminopyridin-2-yl)amino]propyl}-3-(2-hydroxyethyl)-1H-imidazol-3-ium, 1-{3-[(3,5-diaminopyridin-2-yl)amino]propyl}-1-methylpiperidinium, 1-{2-[(3,5-diaminopyridin-2-yl)amino]ethyl}-1-methylpyrrolidinium, 1-{3-[(3,5-diaminopyridin-2-yl)amino]propyl}-1-methylpyrrolidinium, 1-{2-[(3,5-diaminopyridin-2-yl)amino]ethyl}-3-methyl-1H-imidazol-3-ium, 4-{3-[(3,5-diaminopyridin-2-yl)amino]propyl}-4-methylmorpholin-4-ium, 4-{2-[(3,5-diaminopyridin-2-yl)amino]ethyl}-4-methylmorpholin-4-ium, 1-[2-({2-[(3,5-diaminopyridin-2-yl)amino]ethyl}amino)ethyl]-1-methylpiperidinium, 1-[2-({2-[(3,5-diaminopyridin-2-yl)amino]ethyl}amino)ethyl]-1-methylpyrrolidinium, 1-[2-({2-[(3,5-diaminopyridin-2-yl)amino]ethyl}amino)ethyl]-3-methyl-1H-imidazol-3-ium, 4-[2-({2-[(3,5-diaminopyridin-2-yl)amino]ethyl}amino)ethyl]-4-methylmorpholin-4-ium, 2-({2-[(3,5-diaminopyridin-2-yl)amino]ethyl}amino)-N,N,N-trimethylethaneammonium, 3-({2-[(3,5-diaminopyridin-2-yl)amino]ethyl}amino)-N,N,N-trimethylpropane-1-ammonium, 2-{2-[(3,5-diaminopyridin-2-yl)amino]ethoxy}-N,N,N-trimethylethaneammonium, 3-{2-[(3,5-diaminopyridin-2-yl)amino]ethoxy}-N,N,N-trimethylpropane-1-ammonium, 1-(2-{2-[(3,5-diaminopyridin-2-yl)amino]ethoxy}ethyl)-1-methylpiperidinium, 1-(2-{2-[(3,5-diaminopyridin-2-yl)amino]ethoxy}ethyl)-1-methylpyrrolidinium, 1-{3-[(3,5-diaminopyridin-2-yl)amino]propyl}-3-methyl-1H-imidazol-3-ium, 1-[3-({2-[(3,5-diaminopyridin-2-yl)amino]ethyl}amino)propyl]-3-methyl-1H-imidazol-3-ium, 4-[3-({2-[(3,5-diaminopyridin-2-yl)amino]ethyl}amino)propyl]-1,1-dimethylpiperazin-1-ium, 1-(3-{2-[(3,5-diaminopyridin-2-yl)amino]ethoxy}propyl)-1-methylpiperidinium, 4-[3-({2-[(3,5-diaminopyridin-2-yl)amino]ethyl}amino)propyl]-4-methylmorpholin-4-ium, 1-[3-({2-[(3,5-diaminopyridin-2-yl)amino]ethyl}amino)propyl]-1-methylpyrrolidinium, 3-({2-[(3,5-diaminopyridin-2-yl)amino]ethyl}amino)-N-ethyl-N-methyl-N-propylpropane-1-ammonium, 3-[(3,5-diaminopyridin-2-yl)amino]-N,N,N-trimethylpropane-1-ammonium, 3-[(3,5-diaminopyridin-2-yl)(methyl)amino]-N,N,N-trimethylpropane-1-ammonium, 3-[(3,5-diaminopyridin-2-yl)oxy]-N,N,N-trimethylpropane-1-ammonium, 1-{2-[(3,5-diaminopyridin-2-yl)amino]ethyl}-3-(2-hydroxyethyl)-1H-imidazol-3-ium, 4-(3,5-diaminopyridin-2-yl)-1-(2-hydroxyethyl)-1-methylpiperazin-1-ium, 4-(3,5-diaminopyridin-2-yl)-1,1-bis(2-hydroxyethyl)piperazin-1-ium, 4-(3,5-diaminopyridin-2-yl)(2-trimethylethane)morpholineammonium, 4-(3,5-diaminopyridin-2-yl)(2-methyldiethylethane)morpholineammonium, 4-(3,5-diaminopyridin-2-yl)-2-morpholine-1,1-dimethylpyrrolidinium, (3,5-diaminopyridin-2-yl)-3-trimethylpiperidineammonium, (3,5-diaminopyridin-2-yl)-4-trimethylpiperidineammonium, 4-(3,5-diaminopyridin-2-yl)(2-trimethylmethane)morpholineammonium, 4-(3,5-diaminopyridin-2-yl)(2-methyldiethylmethane)morpholineammonium.

9. Process for synthesizing a cationic aminopyridine of general formula (I') starting with a compound of formula (III):

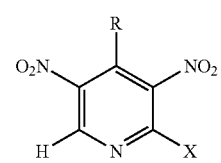

in which X represents a halogen or a group $SO_2R_3$ with $R_3$ chosen from $C_1$-$C_4$ alkyls, the phenyl radical and a methylphenyl radical, and R is chosen from a hydrogen atom, halogens chosen from fluorine, chlorine and bromine, and linear or branched $C_1$-$C_4$ alkyl, carboxyl (—COOH) and ($C_1$-$C_4$) alkoxycarbonyl radicals, the said process comprising at least the following steps, in this order:

substitution of the group X with a group $Z_1R_1$ as defined in claim 1, reduction of the nitro groups.

10. Compounds of formula (II):

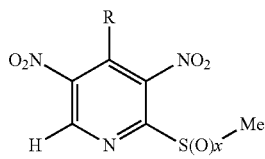

in which R is chosen from a hydrogen atom, halogens chosen from fluorine, chlorine and bromine, and linear or branched $C_1$-$C_4$ alkyl, carboxyl (—COOH) and ($C_1$-$C_4$)alkoxycarbonyl radicals,
and x represents 1 or 2.

11. Ready-to-use cosmetic dye composition comprising, in a suitable dyeing medium;
   at least one oxidation base,
   at least one cationic coupler of general formula (I), acid-addition salts thereof and solvates thereof:

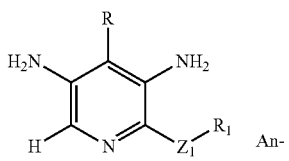

in which the group $Z_1$ $R_1$ is cationic,
$Z_1$ is an oxygen atom or a group $NR_2$;
$R_2$ is a hydrogen atom or a linear or branched $C_1$-$C_4$ alkyl radical, a benzyl radical or an acetyl radical;
$R_1$ is a linear or branched saturated $C_1$-$C_4$ alkyl radical, substituted or intterrupted with a cationic radical, optionally interrupted with one or more oxygen atoms andl/or with one or more groups $NR_2$, optionally substituted with one or more radicals chosen from hydroxyl and $C_1$-$C_4$ alkoxy or hydroxyalkyl radicals, the said cationic radical being as linear, branched or cyclic, saturated or unsaturated radical, comprising a quaternary ammonium, or $R^1$ is a saturated, unsaturated or aromatic, 5- to 8-membered cationic heterocycle optionally snbstatuted with one or more radicals chosen from $C_1$-$C_4$ alkyl, hydroxyl, $C_1$-$C_4$ alkoxy, amino, ($C_1$-$C_4$) alkylamino, di($C_1$-$C_4$)akylamino, thio, ($C_1$-$C_4$)alkylthio, carboxyl, ($C_1$-$C_4$)alkylcarhonyl, suifortyl, amido and $C_1$-$C_4$hydroxyalkyl radicals;
when $Z_1$ represents: $NR_2$ then
$R_1$ and $R_2$ may form, together with the nitrogen atom to which they are attached, an unsaturated 5- to 8-membered cationic heterocycle, optionally sub with one or more radicals chosen from ($C_1$-$C_{10}$) alkyl, hydroxyl, $C_1$-$C_4$ alkoxy, amino, ($C_1$-$C_4$)alkylaniino, di($C_1$-$C_4$)alkylamino, thio, ($C_1$-$C_4$)alkylthio, carboxyl, ($C_1$-$C_4$)atkylcarbonyl, sulfonyl, amido and $C_1$-$C_4$ hydroxyalkyl radical, this heterocycle possibly containing one or more heteroatoms chosen from N and O, or
R1 and R2 may form, together with the nitrogen atom to which they are attached, a saturated or unsaturated 5- to 8-membered non-cationic heterocycle, substituted with a cationic radical and optionally substituted with one or more radicals chosen from $C_1$-$C_{10}$ alkyl, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals; the said cationic radical being a linear, branched or cyclic, saturated or unsaturated radical, comprising a quaternary ammonium;
R is chosen from a hydrogen atom, halogens chosen from fluorine, chlorine and bromine, and linear or branched $C_1$-$C_4$, alkyl, carboxyl (—COOH) and ($C_1$-$C_4$)alkoxycarbonyl radicals,
An—represents an anion or a mixture of anions,
and at least one oxidizing agent.

12. Ready-to-use cosmetic dye composition according to claim 11 wherein the cationic coupler of formula (I) is such $Z_1$ is a group $NR_2$ and $R_1$ and $R_2$ form, together with the nitrogen atom to which they are attached, a saturated or unsaturated 5- to 8-membered cationic heterocycle, selected from piperidinium, imidazolium, pyrrolidinium, morpholinium or piperazinium radical substituted with one or more radicals chosen from $C_1$-$C_4$ hydroxyalkyl and $C_1$-$C_4$ alkyl radicals.

13. Ready-to-use cosmetic dye composition according to claim 11 wherein the cationic coupler of formula (I) IS

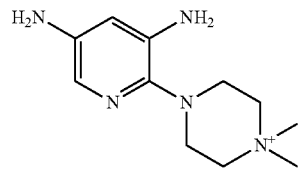 [SMILES: C[N+]1(C)CCN(c2ncc(N)cc2N)CC1]

4-(3,5-diaminopyridin-2-yl)-1,1-dimethylpiperazin-1-ium, An-.

14. Ready-to-use cosmetic dye composition according to claim 11 wherein the oxidizing agent is chosen from hydrogen peroxide, urea peroxide, alkali metal bromates, persalts, peracids and oxidase enzymes.

15. Process for dyeing keratin fibres, characterized in that a cosmetic dye composition comprising, in a suitable dyeing medium, at least one cationic aminopyridine as defined in claim 1 is applied to the said fibres for a time sufficient to develop the desired coloration in the presence of an oxidizing agent, the oxidizing agent being applied before, simultaneously with or after the composition.

16. Multi-compartment device, a first compartment containing the cosmetic composition for dyeing keratin fibres as defined in claim 11, and a second compartment containing an oxidizing agent.

* * * * *